United States Patent [19]

Honma et al.

[11] Patent Number: 5,268,377
[45] Date of Patent: Dec. 7, 1993

[54] IMIDAZOINDOLIZINE DERIVATIVES PROCESS FOR PREPARATION THEREOF AND USE THEREOF TO TREAT HYPERTENSION

[75] Inventors: Yasushi Honma, Ageo; Yasuo Sekine, Kawaguchi; Sumihiro Nomura, Kasukabe; Kazuaki Naito, Tokyo; Hiroshi Narita, Urawa, all of Japan

[73] Assignee: Tanabe Seiyaku Co., Ltd., Osaka, Japan

[21] Appl. No.: 939,652

[22] Filed: Sep. 3, 1992

[30] Foreign Application Priority Data

Sep. 10, 1991 [JP] Japan .................................. 3-308560
Jan. 27, 1992 [JP] Japan .................................. 4-053044

[51] Int. Cl.$^5$ .................. A61K 31/395; C07D 471/14; C07D 515/12; C07D 515/14
[52] U.S. Cl. ..................................... 514/293; 546/82; 548/302.1
[58] Field of Search .................. 546/82; 514/293; 548/302.1

[56] References Cited

U.S. PATENT DOCUMENTS 4,686,226 8/1987 Huff et al. .......................... 546/82
4,816,463 3/1989 Blankley et al. ..................... 514/293

FOREIGN PATENT DOCUMENTS 0253310 1/1988 European Pat. Off. ............. 514/293
0392317 10/1990 European Pat. Off. .
0426021 5/1991 European Pat. Off. ............. 514/293
1047148 12/1986 U.S.S.R. .

OTHER PUBLICATIONS

Wong et al., Cardiovascular Drug Reviews, vol. 9, No. 4, pp. 317–339 (1991).

*Primary Examiner*—Floyd D. Higel
*Attorney, Agent, or Firm*—Birch, Stewart, Kolasch & Birch

[57] ABSTRACT

An inidazoindolizine derivative of the formula [I]:

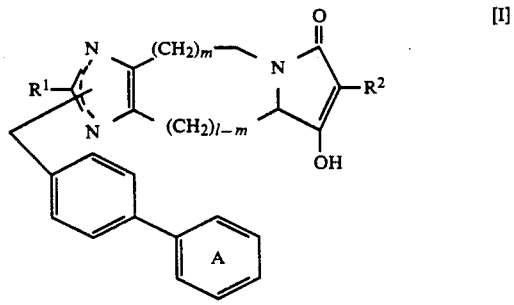

wherein $R^1$ is lower alkyl, $R^2$ is hydrogen, cyano, lower alkyl, lower alkanoyl, lower alkoxycarbonyl, phenyl-lower alkoxycarbonyl, lower alkylsulfonyl, substituted or unsubstituted phenyl, arylcarbonyl, or 5- or 6-membered nitrogen-containing heteromonocyclic group-substituted carbonyl, Ring A is substituted or unsubstituted phenyl, and m is 0 or 1, or a pharmaceutically acceptable salt thereof, and process for preparation thereof, said imidazoindolizine derivatives and pharmaceutically acceptable salts thereof show excellent angiotensin II inhibitory activities and are useful in the prophylaxis or treatment of hypertension.

26 Claims, No Drawings

IMIDAZOINDOLIZINE DERIVATIVES PROCESS FOR PREPARATION THEREOF AND USE THEREOF TO TREAT HYPERTENSION

The present invention relates to novel imidazoindolizine derivatives having a hypotensive activity, and process for preparation thereof.

PRIOR ART

Angiotensin II is a biologically active peptide consisting of eight amino acids, which is produced by specific conversion of angiotensin I by an angiotensin converting enzyme during circulation mainly in the lung. Said angiotensin II constricts vascular smooth muscle as well as promotes the secretion of aldosterone in the adrenal cortex, by which angiotensin II increases blood pressure. Therefore, it is well known that angiotensin II receptor antagonists may be useful in the treatment of hypertension.

Based on the above-mentioned mechanism of action, there have been known some hypotensive agents, for example, 2-n-butyl-4-chloro-5-hydroxymethyl-1-{2'-(1H-tetrazol-5-yl)biphenyl-4-yl}methylimidazole, and the like [cf. European Patent Publication No. 253310/S], but these conventional hypotensive agents are all the compounds having a monocyclic nucleus, i.e. imidazole nucleus.

BRIEF DESCRIPTION OF THE INVENTION

An object of the present invention is to provide novel imidazoindolizine derivatives and pharmaceutically acceptable salts thereof, which show potent angiotensin II inhibitory activities and are useful as a hypotensive agent. Another object of the invention is to provide a process for preparing the said imidazoindolizine derivatives.

DETAILED DESCRIPTION OF THE INVENTION

The present invention relates to imidazoindolizine derivatives of the following formula [I], and pharmaceutically acceptable salts thereof, and further relates to a process for preparing the same.

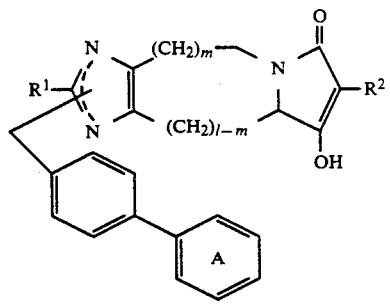

wherein $R^1$ is a lower alkyl group, $R^2$ is hydrogen atom, cyano group, a lower alkyl group, a lower alkanoyl group, a lower alkoxycarbonyl group, a phenyl-lower alkoxycarbonyl group, a lower alkylsulfonyl group, a substituted or unsubstituted phenyl group, an arylcarbonyl group, or a 5- or 6-membered nitrogen-containing heteromonocyclic group-substituted carbonyl group, Ring A is a substituted or unsubstituted phenyl group, and m is 0 or 1.

Preferred examples of the present compounds [I] are compounds of the above formula [I], wherein $R^1$ is an alkyl group having 1 to 6 carbon atoms, preferably 1 to 4 carbon atoms, $R^2$ is hydrogen atom; cyano group; an alkyl group having 1 to 6 carbon atoms, preferably 1 to 4 carbon atoms; an alkanoyl group having 2 to 6 carbon atoms, preferably 2 to 4 carbon atoms; an alkoxycarbonyl group having 1 to 6 carbon atoms, preferably 1 to 4 carbon atoms in the alkoxy moiety; an alkoxycarbonyl group having 1 to 6 carbon atoms, preferably having 1 to 4 carbon atoms in the alkoxy moiety which is substituted by a phenyl group; an alkylsulfonyl group having 1 to 6 carbon atoms, preferably 1 to 4 carbon atoms; a phenyl group which may optionally be substituted by a group selected from a halogen atom, hydroxy group, carboxyl group, an alkyl group having 1 to 6 carbon atoms, preferably 1 to 4 carbon atoms, an alkoxy group having 1 to 6 carbon atoms, preferably 1 to 4 carbon atoms, an alkoxycarbonyl group having 1 to 6 carbon atoms, preferably 1 to 4 carbon atoms in the alkoxy moiety and carbamoyl group; an arylcarbonyl group having 6 to 15 carbon atoms, preferably 6 to 10 carbon atoms in the aryl moiety; or a 5-or 6-membered nitrogen-containing heteromonocyclic group-substituted carbonyl group, and Ring A is a phenyl group which may optionally be substituted by a protected or unprotected tetrazolyl group, a protected or unprotected carboxyl group and an alkylsulfonylamino group having 1 to 6 carbon atoms, preferably 1 to 4 carbon atoms.

Preferred compounds [I] in view of the excellent pharmacological activity are compounds of the formula [I] wherein $R^1$ is a lower alkyl group, $R^2$ is cyano group; a lower alkanoyl group; a lower alkoxycarbonyl group; a phenyl-lower alkoxycarbonyl group; a phenyl group which may optionally be substituted by a halogen atom; an arylcarbonyl group, and Ring A is tetrazolylphenyl group or carboxyphenyl group.

More preferred compounds as a medicament are compounds of the formula [I] wherein $R^1$ is ethyl group, n-propyl group or n-butyl group, $R^2$ is cyano group, acetyl group, methoxycarbonyl group, ethoxycarbonyl group, benzyloxycarbonyl group, chlorophenyl group or benzoyl group, and Ring A is tetrazolylphenyl group or carboxyphenyl group.

The compounds [I] of the present invention may be used as a medicament either in the form of a free base or a pharmaceutically acceptable salt thereof. The pharmaceutically acceptable salts are, for example, alkali metal salts (e.g. sodium salt, potassium salt, etc.), alkaline earth metal salts (e.g. calcium salt, magnesium salt, etc.), heavy metal salts (e.g. zinc salt, etc.), and organic amine salts (e.g. ammonium salt, triethylamine salt, pyridine salt, ethanolamine salt, a basic amino acid salt, etc.). These salts may easily be prepared by treating the compounds [I] with the corresponding inorganic or organic base in an appropriate solvent.

The compounds [I] of the present invention may exist in the form of two position isomers of the frmulae [I-a] and [I-b], and the present invention also includes these isomers.

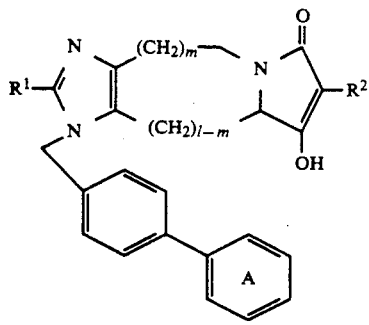

[I-a]

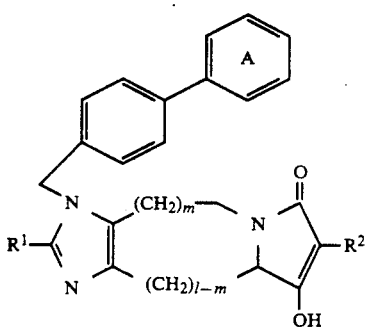

[I-b]

wherein the sumbols are the same as defined above. The compounds [I] of the present invention also exist in the form of optically active isomers due to an asymmetric carbon atom thereof, and the present invention also includes these optically active isomers and a mixture thereof.

The compounds [I] of the present invention and pharmaceutically acceptable salts thereof my be administered either orally or parenterally and may also be used in the form of a pharmaceutical preparation in admixture with pharmaceutically acceptable excipients suitable for oral administration or parenteral administration. The pharmaceutical preparations may be in solid form such as tablets, capsules, powders, etc., or in liquid form such as solutions, suspensions, emulsions, etc. When administered parenterally, it may be used in the form of injection preparations.

The daily dose of the compounds [I] of the present invention and pharmaceutically acceptable salts thereof varies depending on age, weight, conditions of patients and severity of diseases, but when administered orally, it is usually in the range of 0.01 to 10 mg/kg, preferably 0.03 to 5 mg/kg, and when administered parenterally, it is usually in the range of 0.002 to 1 mg/kg, preferably 0.01 to 0.3 mg/kg.

According to the present invention, the compounds [I] can be prepared by subjecting an imidazopyridine compound of the formula [II]:

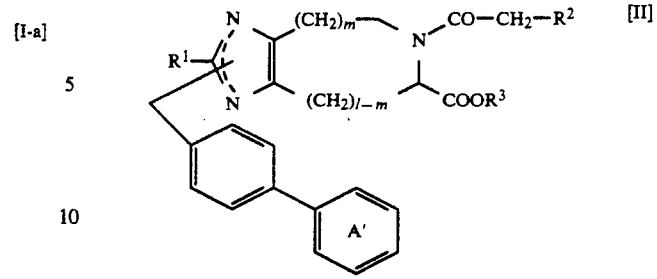

[II]

wherein a group of the formula: —COOR$^3$ is a protected or unprotected carboxyl group, Ring A' is a substituted or unsubstituted phenyl group, and other symbols are the same as defined above, or a salt thereof to intramolecular cyclization reaction, and when Ring A' is a phenyl group substituted by a protected tetrazolyl group or a protected carboxyl group, followed by removing the said protecting group, if necessary.

In the above intramolecular cyclization reaction, the protecting group ($R^3$) for the compound [II] may be any group which can be easily removed in the form of an alcohol, and includes, for example, an alkyl group having 1 to 6 carbon atoms, preferably 1 to 4 carbon atoms such as methyl group, ethyl group, and the like, or an alkyl having 1 to 6 carbon atoms, preferably 1 to 4 carbon atoms which is substituted by a phenyl group such as benzyl group, and the like.

The salts of the compounds [II] are, for example, alkali metal salts and alkaline earth metal salts.

The intramolecular cyclization reaction can preferably be carried out in the presence of a base in a suitable solvent. The base includes, for example, alkali metal hydroxides, alkali metal hydrides, alkali metal hydrogen carbonates, alkyl-substituted alkali metal amides, lower alkyl alkali metals, alkali metal alkoxides, and alkali metals. In case of using an alkali metal as a base, the suitable solvent includes, for example, benzene, toluene, or a mixture thereof, and in case of using a base other than alkali metals, the solvent includes, for example, in addition to the above solvents, water, tetrahydrofuran, a lower alkanol or a mixture thereof. The reaction is preferably carried out under cooling or heating, for example, at a temperature of −30° C. to 100° C., preferably at room temperature.

Among the compounds [I] of the present invention, the compounds wherein Ring A is tetrazolylphenyl group or carboxyphenyl group can be prepared by subjecting the compounds [II] wherein Ring A' is a protected tetrazolyl-substituted phenyl group or a protected carboxyl-substituted phenyl group to the same intramolecular cyclization reaction as above, followed by removing the said protecting group simultaneously or after the intramolecular cyclization reaction.

The protecting group may be any conventional ones, for example, the protecting group for tetrazolyl group is trityl, and the like, and the protecting group for carboxyl group is the same groups as ones for $R^3$ as mentioned above. The removal of these protecting groups may be carried out by any conventional method such as hydrolysis, reduction, and the like, which is selected depending on the kind of the protecting group to be removed.

The above reactions proceed without racemization, and hence, the optically active compound [I] can be obtained by the intramolecular cyclization reaction of the optically active starting compound [II].

Besides, the starting compounds [II] of the present invention are novel compounds, and can be prepared, for example, by reacting an imidazopyridine compound of the formula [III]:

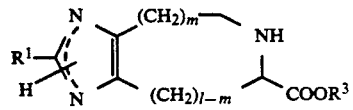

wherein the symbols are the same as defined above, which is prepared by the method disclosed in Japanese Patent First Publication (KOKAI) No. 167687/1986 or Japanese Patent First Publication (KOKAI) No. 101062/1990, with a biphenyl compound of the formula [IV]:

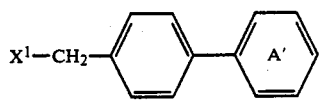

wherein $X^1$ is a halogen atom, and Ring A' is the same as defined above, in the presence of an acid acceptor (e.g. sodium hydroxide, potassium t-butoxide, etc.), during which the imino group adjacent to the carboxyl group of the compound [III] is protected, followed by removing the protecting group for the imino group to give an imidazopyridine compound of the formula [V]:

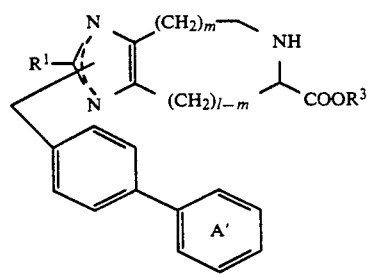

wherein the symbols are the same as defined above, and further by reacting the compound [V] or a salt thereof (e.g. alkali metal salt, alkaline earth metal salt, etc.) with a free carboxylic acid compound of the formula [VI]:

HOOCCH$_2$—R$^2$ [VI]

wherein $R^2$ is the same as defined above, in the presence of a conventional dehydrating agent, or by reacting the compound [V] or a salt thereof with a reactive derivative of the carboxylic acid compound [VI] (e.g. acid halide, active ester, etc.) in the presence or absence of an acid acceptor (e.g. triethylamine, etc.). The starting compound [II] wherein $R^2$ is acetyl group can also be prepared by reacting the compound [V] with diketene.

The starting compound [II] can also be prepared by reacting an imidazole compound of the formula [VII]:

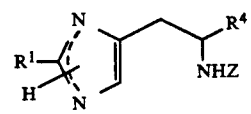

wherein Z is a protecting group for an amino group, $R^4$ is hydrogen atom or a group of the formula: —COOR$^3$, and $R^1$ and the group of the formula: —COOR$^3$ are the same as defined above, which is prepared according to the method disclosed in European Journal of Medicinal Chemistry, Vol. 10, No. 2, pp. 129-133 (1975), with the biphenyl compound of the formula [IV] in the same manners as above, and after removing the protecting group (Z) for amino group, followed by (i) in case that $R^4$ of the product is a group of the formula: —COOR$^3$, reacting the product with formalin in the presence of a mineral acid (e.g. hydrochloric acid, etc.), or (ii) in case that $R^4$ of the product is hydrogen atom, reacting the product with glyoxylic acid or ester of glyoxylic acid in the presence or absence of a mineral acid (e.g. hydrochloric acid, etc.) or an alkali (e.g. sodium hydroxide, etc.), and if necessary, by esterification of the carboxyl group in a conventional manner, and further by reacting the obtained imidazopyridine compound with the compound [VI] or a reactive derivative thereof in the same manner as above.

In the above reaction, the protecting group (Z) for amino group may be any conventional one, and in case that Ring A' of the compound [IV] is tetrazolylphenyl group or carboxyphenyl group, it is preferable to protect said tetrazolyl group or carboxyl group with a conventional protecting group.

The optically active starting compound [II] may be prepared, for example, by subjecting the racemic mixture of the compound [II] to column chromatography for separation of optically active isomers.

Besides, in the compounds [II], [III], [V] and [VII], the partial structure of the formula:

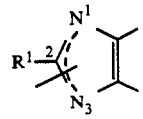

indicates the structures of the following formulae:

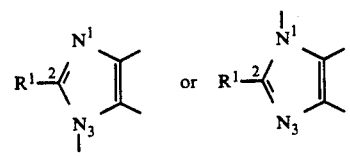

EXAMPLES

The present invention is illustrated by the following Examples and Reference Examples, but should not be construed to be limited thereto.

Example 1

(1) Methyl 2-n-butyl-5-benzyloxycarbonyl-1-{2'-(1-trityl-1H-tetrazol-5-yl)biphenyl-4-yl}methyl-4,5,6,7-tetrahydroimidazo[4,5-c]pyridine-6-carboxylate (1.26 g)

and a catalytic amount of 10 % palladium-carbon are added to methanol (300 ml), and the mixture is stirred under hydrogen atmosphere. After the reaction is completed, palladium-carbon is removed by filtration, and the filtrate is evaporated under reduced pressure to give methyl 2-n-butyl-1-{2'-( 1-trityl-1H-tetrazol-5-yl)biphenyl-4-yl}methyl-4,5,6,7-tetrahydroimidazo[4,5-c]pyridine-6-carboxylate (0.94 g) as foam.

NMR (CDCl$_3$)δ: 0.86 (3H, t), 3.68 (3H, s), 4.86 (2H, s)

(2) The above product (0.96 g) is dissolved in methylene chloride (25 ml), and thereto is added triethylamine (0.2 g). To the miture is added dropwise ethoxycarbonylacetyl chloride (0.22 ml) under ice-cooling, and the mixture is stirred at room temperature for two hours. Chloroform and water are added to the mixture. The aqueous layer is extracted with chloroform, and the washings and the chloroform layer are combined, dried, and then the solvent is distilled off. The residue is purified by silica gel column chromatography (solvent; ethyl acetate/chloroform) to give methyl 2-n-butyl-5-ethoxycarbonylacetyl-1-{2'-(1-trityl-1H-tetrazol-5-yl)biphenyl-4-yl}methyl-4,5,6,7-tetrahydroimidazo[4,5-c]pyridine-6-carboxylate (0.74 g) as colorless oil.

NMR (CDCl$_3$)δ: 0.86 (3H, t), 4.56 (2H, s), 4.87 (2H, ABq)

(3) The above product (0.67 g) is dissolved in tetrahydrofuran (2 ml), and thereto is added 90 % formic acid (5 ml), and the mixture is stirred at room temperature for four hours. The mixture is evaporated under reduced pressure to remove the solvent, and the resulting residue is dissolved in methanol (20 ml), and thereto is added 1N aqueous sodium hydroxide solution (4.8 ml). The mixture is stirred at room temperature overnight, and the solvent is distilled off. To the residue are added water and ether. The aqueous layer is evaporated under reduced pressure, and the resulting oil is purified by column chromatography of nonionic adsorbing resin (tradename; HP-20, manufactured by Mitsubishi Kasei Corporation) and lyophilized to give 2-n-butyl-7-ethoxycarbonyl-8-hydroxy-1-{2'-(1H-tetrazol-5-yl)biphenyl-4-yl}methyl-1,4,8a,9-tetrahydro-6H-imidazo[4,5-f]indolizin-6-one disodium salt (0.39 g) as powder.

NMR (DMSO-d$_6$)δ: 0.84 (3H, t), 1.15 (3H, t), 4.02 (2H, q), 5.07 (2H, s)

Example 2

(1) A mixture of methyl 2-n-butyl-1-{2'-(1-trityl-1H-tetrazol-5-yl)biphenyl-4-yl}methyl-4,5,6,7-tetrahydroimidazo[4,5-c]pyridine-6-carboxylate (0.81 g), dicyclohexyl-carbodiimide (0.26 g), 1-hydroxybenzotriazole (0.17 g), cyanoacetic acid (0.11 g) and acetonitrile (10 ml) is stirred at room temperature overnight. After the reaction is completed, ethyl acetate is added to the reaction mixture, and the mixture is waehed with aqueous sodium hydrogen carbonate solution, dried, and the solvent is distilled off under reduced pressure. The resulting residue is purified by silica gel column chromatography (solvent; ethyl acetate) to give methyl 2-n-butyl-5-cyanoacetyl-1-{2'-(1-trityl-1H-tetrazol-5-yl)biphenyl-4-yl}methyl-4,5,6,7-tetrahydroimidazo[4,5-c]pyridine-6-carboxylate (0.83 g) as foam.

NMR (CDCl$_3$)δ: 0.87 (3H, t), 3.61 (3H, s), 3.63 (2H, s), 4.88 (2H, ABq)

(2) The above product is treated in the same manner as in Example 1-(3) to give 2-n-butyl-7-cyano-8-hydroxy-1-{2'-(1H-tetrazol-5-yl)biphenyl-4-yl}methyl-1,4,8a,9-tetrahydro-6H-imidazo[4,5-f]indolizin-6-one disodium salt.

NMR (DMSO-d$_6$)δ: 0.84 (3H, t), 5.06 (2H, s)

Example 3

(1) Methyl 2-n-butyl-5-benzyloxycarbonyl-3-{2'-(1-trityl-1H-tetrazol-5 yl)biphenyl-4-yl}methyl-4,5,6,7-tetrahydroimidazo[4,5-c]pyridine-6-carboxylate is treated in the same manner as in Example 1-(1) to give methyl 2-n-butyl-3-552'-(1-trityl-1H-tetrazol 5-yl)biphenyl-4-yl}methyl-4,5,6,7-tetrahydroimidazo[4,5-c]pyridine-6-carboxylate.

NMR (CDCl$_3$)δ: 0.87 (3H, t), 3.75 (3H, s), 4.81 (2H, s)

(2) The above product and methoxycarbonylacetyl chloride are treated in the same manner as in Example 1-(2) to give methyl 2-n-butyl-5-methoxycarbonylacetyl-3-{2'-(1-trityl 1H-tetrazol-5-yl)biphenyl-4-yl}methyl-4,5,6,7-tetrahydroimidazo[4,5-c]pyridine-6-carboxylate.

(3) The above produce is treated in the same manner as in Example 1-(3) to give 2-n-butyl-7-methoxycarbonyl-8-hydroxy-3-{2'-(1H-tetrazol-5-yl)biphenyl-4-yl}methyl-1,4,8a,9-tetrahydro-6H-imidazo[4,5-f]indolizin-6-one disodium salt.

NMR (DMSO-d$_6$)δ; 0.84 (3H, t), 5.06 (2H, ABq)

Example 4

(1) Methyl 2-n-butyl-3-{2'-(1-trityl-1H-tetrazol-5-yl)biphenyl-4-yl}methyl-4,5,6,7-tetrahydroimidazo[4,5-c]-pyridine-6-carboxylate and ethoxycarbonylacetyl chloride are treated in the same manner as in Example 1-(2) to give methyl 2-n-butyl-5-ethoxycarbonylacetyl-3-{2'-(1-trityl-1H-tetrazol-5-yl)biphenyl-4-yl}methyl-4,5,6,7-tetrahydroimidazo[4,5-c]pyridine-6-carboxylate.

NMR (CDCl$_3$)δ: 0.81–0.91 (3H, m), 4.80 (2H, br0s)

(2) The above produce is treated in the same manner as in Example 1-(3) to give 2-n-butyl-7-ethoxycarbonyl-8-hydroxy-3-{2'-(1H-tetrazol-5-yl)biphenyl-4-yl}-methyl-1,4,8a,9-tetrahydro-6H-imidazo[4,5-f]indolizin-6-one disodium salt.

NMR (DMSO-d$_6$)δ: 0.84 (3H, t), 1.15 (3H, t), 4.02, (2H, q), 5.07 (2H, s)

Example 5

(1) Methyl 2-n-butyl-3-{2'-(1H-tetrazol-5-yl)-biphenyl-4-yl}methyl-4,5,6,7-tetrahydroimidazo[4,5-c]pyridine-4-carboxylate and ethoxycarbonylacetyl chloride are treated in the same manner as in Example 1-(2) to give methyl 2-n-butyl-5-ethoxycarbonylacetyl-3-{2'-(1H-tetrazol-5-yl)biphenyl-4-yl}methyl-4,5,6,7-tetrahydroimidazo[4,5-c]pyridine-4-carboxylate.

NMR (CHCl$_3$)δ: 0.95 (3H, t), 1.18 (3H, t), 3.50 (2H, s), 5.28 (2H, ABq), 5.40 (1H, s)

(2) The above product (0.24 g) is dissolved in ethanol (15 ml), and thereto is added sodium hydride (oil-dispersion type) (0.035 g), and the mixture is stirred at room temperature overnight. The solvent is distilled off under reduced pressure, and the resulting residue is purified by column chromatogrpahy of nonionic adsorbing resin (tradename; HP-20, manufactured by Mitsubishi Kasei Corporation) and lyophilized to give 2-n-butyl-8-ethoxycarbonyl-9-hydroxy-1-{2'-(1H-tetrazol-5-yl)biphenyl-4-yl}-methyl-1,4,5,9a-tetrahydro-7H-imidazo[4,5-g]indolizin-7-one disodium salt (0.15 g).

NMR (DMSO-d$_6$)δ: 0.81 (3H, t), 1.15 (3H, t), 4.41 (1H, s)

Example 6

(1) To a mixture of methyl 2-n-butyl-5-ethoxycarbonylacetyl-3-{2'-(1H-tetrazol-5-yl)biphenyl-4-yl}methyl-4,5,6,7-tetrahydroimidazo[4,5-c]pyridine-4- carboxylate (2.0 g), triethylamine (0.69 g) and chloroform (20 ml) is added trityl chloride (1.43 g), and the mixture is stirred at room temperature for 30 minutes. The reaction solution is washed, dried and evaporated under reduced pressure to remove the solvent The resulting residue is purified by silica gel column chromatography (solvent; ethyl acetate/n-hexane) to give methyl 2-n-butyl-5-ethoxycarbonylacetyl-3-{2 -(1-trityl-1H-tetrazol-5-yl)biphenyl-4-yl}methyl-4,5,6,7-tetrahydroimidazo[4,5-c]pyridine-4-carboxylate (1.29 g) as needles.

m.p. 124°–126° C. (decomposed)

(2) The above product is resolved by HPLC column for separation of optically active isomers (tradename; Chiralcel OD, manufactured by Daicel Chemical Industries, Ltd.) (solvent; n-hexane/ethanol=7:3) to give (+)-isomer and (−)-isomer, separately.

(+)-Isomer $[\alpha]_D$: +25.2° (c=0.5, chloroform, 25° C.)

(−)-Isomer:

$[\alpha]_D$: −22.8° (c=0.5, chloroform, 25° C.)

(3) To a mixture of methyl (+)-2-n-butyl-5-ethoxycarbonylacetyl-3-{2'-(1-trityl-1H-tetrazol-5-yl)biphenyl-4-yl}methyl-4,5,6,7-tetrahydroimidazo[4,5-c]pyridine-4-carboxylate (395 mg) and tetrahydrofuran (4 ml) is added 90% formic acid (8 ml) under ice-cooling, and the mixture is stirred at room temperature for 30 minutes, and evaporated under reduced pressure to remove the solvent. The resulting residue is purified by silica gel column chromatography (solvent; chloroform/methanol) to give methyl (+)-2 -n-butyl-5-ethoxycarbonylacetyl-3-{2'-(1H-tetrazol-5-yl)biphenyl-4-yl}methyl-4,5,6,7-tetrahydroimidazo[4,5-c]pyridine-4-carboxylate (270 mg) as foam.

$[\alpha]_D$: +70.4° (c=0.5, chloroform, 20° C.)

(4) To a mixture of the above product (270 mg), ethanol (3.5 ml) and water (1.5 ml) is added sodium hydrogen carbonate (77 mg), and the mixture is stirred at 60° C. for one hour, and evaporated under reduced pressure to remove the solvent. The resulting residue is purified by column chromatography of nonionic adsorbing resin (tradename; HP-20, manufactured by Mitsubishi Kasei Corporation) and lyophilized to give (−)-2-n-butyl-8-ethoxycarbonyl-9-hydroxy-1-{2'-(1H-tetrazol-5-yl)biphenyl-4-yl}methyl-1,4,5,9a-tetrahydro-7H-imidazo[4,5-g]indolizin-7-one disodium salt (244 mg) as powder.

$[\alpha]_D$ −165° (c=0.42, methanol, 20° C.)

Example 7

(1) Methyl (-)-2-n-butyl-5-ethoxycarbonylacetyl-3-{2'-(1-trityl-1H-tetrazol-5-yl)biphenyl-4-yl}methyl-4,5,6,7-tetrahydroimidazo[4,5-c]pyridine-4-carboxylate is treated in the same manner as in Example 6-(3) to give methyl (−)-2-n-butyl-5-ethoxycarbonylacetyl-3-{2'-(1H-tetrazol-5-yl)-biphenyl-4-yl}methyl-4,5,6,7-tetrahydroimidazo[4,5-c]-pyridine-4 carboxylate as foam.

$[\alpha]_D$: −70.8° (c=0.5, chloroform, 20° C.)

(2) The above product is treated in the same manner as in Example 6-(4) to give (+)-2-n-butyl-8-ethoxycarbonyl-9-hydroxy-1-{2'-(1H-tetrazol-5-yl)biphenyl-4-yl}methyl-1,4,5,9a-tetrahydro-7H-imidazo[4,5-g]indolizin-7-one disodium salt as powder.

$[\alpha]_D$: +162° (c=0.42, methanol, 20° C.)

Example 8

(1) A mixture of methyl 2-n-propyl-3-{2'-(1H-tetrazol-5-yl)biphenyl-4-yl}methyl-4,5,6,7-tetrahydroimidazo[4,5-c]pyridine-6-carboxylate hydrochloride (0.53 g), ethoxycarbonylacetic acid (0.32 g), 1-hydroxybenzotriazole (0.32 g), triethylamine (0.335 ml), 1-ethyl-3-(3-dimethylaminopropyl)carbodiimide hydrochloride (0.46 g) and methylene chloride (10 ml) is stirred at room temperature overnight. The reaction solution is washed, dried, and evaporated to remove the solvent. The resulting oily residue is purified by silica gel column chromatography (solvent; chloroform/methanol) to give methyl 2-n-propyl-5-ethoxycarbonylacetyl-3-[2'-(1H-tetrazol-5-yl)biphenyl-4-yl]-methyl-4,5,6,7-tetrahydroimidazo[4,5-c]pyridine-6-carboxylate (0.33 g) as colorless foam.

NMR (CDCl$_3$)δ: 0.93 (3H, t), 1.14–1.28 (3H, m), 3.43–3.50 (2H, m), 3.65 and 3.68 (3H, each s)

(2) The above product is treated in the same manner as in Example 5-(2) except that the reaction is carried out for 15 minutes to give 2-n-propyl-7-ethoxycarbonyl-8-hydroxy-3-{2'-(1H-tetrazol-5-yl)biphenyl-4 -yl]-methyl-1,4,8a,9-tetrahydroimidazo[4,5-f]indolizin-6-one disodium salt as powder.

NMR (DMSO-d$_6$)δ: 0.90 (3H, t), 5.07 (2H, ABq)

Example 9

(1) Methyl 2-n-butyl-3-{2'-(1H-tetrazol-5-yl)-biphenyl-4-yl}methyl-4,5,6,7-tetrahydroimidazo[4,5-c]-pyridine-6-carboxylate hydrochloride and cyanoacetic acid are treated in the same manner as in Example 8-(1) to give methyl 2-n-butyl-5-cyanoacetyl-3-{2'-(1H-tetrazol-5-yl)-biphenyl-4-yl}methyl-4,5,6,7-tetrahydroimidazo[4,5-c]-pyridine-6-carboxylate.

IR $_{max}$$^{Nujol}$ ν(cm$^{-1}$): 1740, 1670

(2) The above product is treated in the same manner as in Example 5-(2) except that the reaction is carried out for 15 minutes to give 2-n-butyl-7-cyano-8-hydroxy-3-{2'-(1H-tetrazol-5-yl)biphenyl-4-yl}methyl-1,4,8a,9-tetrahydroimidazo[4,5-f]indolizin-6-one disodium salt as powder.

NMR (DMSO-d$_6$)δ: 0.84 (3H, t), 5.06 (2H, s)

Example 10

(1) Methyl 2-n-butyl-3-{2'-(1H-tetrazol-5-yl)-biphenyl-4-yl}methyl-4,5,6,7-tetrahydroimidazo[4,5-c]-pyridine 6-carboxylate hydrochloride and benzyloxycarbonyl-acetic acid are treated in the same manner as in Example 8-(1) to give methyl 2-n-butyl-5-benzyloxycarbonylacetyl-3 -{2'-(1H-tetrazol-5-yl)biphenyl-4-yl}methyl-4,5,6,7-tetra-hydroimidazo[4,5-c]pyridine-6-carboxylate.

IR$_{max}$$^{Nujol}$ν(cm$^{-1}$): 1740, 1660

(2) The above product is treated in the same manner as in Example 5-(2) except that the reaction is carried ot for 15 minutes to give 2-n-butyl-7-benzyloxycarbonyl-8-hydroxy-3-(2'-(1H-tetrazol-5-yl)biphenyl-4-yl]-methyl-1,4,8a,9-tetrahydroimidazo[4,5-f]indolizin-6-one disodium salt as powder.

NMR (DMSO-d$_6$)δ: 0.84 (3H, t), 5.10 (2H, s)

Example 11

(1) Methyl 2-n-butyl-3-{2'-(1H-tetrazol-5-yl)-biphenyl-4-yl}methyl-4,5,6,7-tetrahydroimidazo[4,5-c]-pyridine-4-carboxylate and cyanoacetic acid are treated in the same manner as in Example 2-(1) to give methyl 2-n-butyl-5-cyanoacetyl-3-(2'-(1H-tetrazol-5-yl)biphenyl-4-yl}-methyl-4,5,6,7-tetrahydroimidazo[4,5-c]pyridine-4-carboxylate.

NMR (CDCl₃)δ: 0.94 (3H, t), 3.67 (2H, s), 3.75 (3H, s), 5.29 (2H, s)

(2) The above product is treated in the same manner as in Example 5-(2) to give 2-n-butyl-8-cyano-9-hydroxy-1-(2'-(1H-tetrazol-5-yl)biphenyl-4-yl]methyl-1,4,5,9a-tetrahydro-7H-imidazo[4,5-g]indolizin-7-one disodium salt.

NMR (DMSO-d₆)δ: 0.81 (3H, t), 4.48 (1H, s)

Example 12

(1) To a mixture of methyl 2-n-butyl-3-{2'-(1H-tetrazol-5-yl)biphenyl-4-yl}methyl-4,5,6,7-tetrahydroimidazo[4,5-c]pyridine-4-carboxylate (0.50 g) and methanol (10 ml) is added diketene (0.20 g), and the mixture is stirred at room temperature for two hours. The solvent is distilled off under reduced pressure, and to the residue is added chloroform. The mixture is washed and dried, and evaporated under reduced pressure to remove the solvent. The resulting residue is purified by silica gel column chromatography (solvent; chloroform/ethyl acetate/methanol) to give methyl 2-n-butyl-5-acetoacetyl-3-{2'-(1H-tetrazol-5-yl)biphenyl-4-yl}methyl-4,5,6,7-tetrahydroimidazo[4,5-c]-pyridine-4-carboxylate (0.29 g) as foam.

NMR (CDCl₃)δ: 0.96 (3H, t), 2.22 (3H, s), 3.74 (3H, s)

(2) The above product is treated in the same manner as in Example 5-(2) except that the reaction is carried out for 15 minutes to give 2-n-butyl-8-acetyl-9-hydroxy-1-{2'-(1H-tetrazol-5-yl)biphenyl-4-yl}methyl-1,4,5,9a-tetrahydro 7H imidazo[4,5-g]indolizin-7-one disodium salt as powder.

NMR (D₂O)δ: 0.78 (3H, t), 2.26 (3H, s), 4.49 (1H, s)

Example 13

(1) Methyl 2-n-propyl-3-{2'-(1H-tetrazol-5-yl)-biphenyl-4-yl]methyl-4,5,6,7-tetrahydroimidazo[4,5-c]-pyridine-4-carboxylate and ethoxycarbonylacetic acid are treated in the same manner as in Example 8-(1) to give methyl 2-n-propyl-5-ethoxycarbonylacetyl-3-(2'-(1H-tetrazol-5-yl)biphenyl-4-yl]methyl-4,5,6,7-tetrahydroimidazo[4,5-c]-pyridine-4-carboxylate.

NMR (CDCl₃)δ: 1.03 (3H, t), 1.18 (3H, t), 3.73 (3H, s)

(2) The above product is treated in the same manner as in Example 5-(2) except that the reaction is carried out for 15 minutes to give 2-n-propyl-8-ethoxycarbonyl-9-hydroxy-1-[2'-(1H-tetrazol-5-yl)biphenyl-4-yl]-methyl-1,4,5,9a-tetrahydro-7H-imidazo[4,5-g]indolizin-7-one disodium salt as powder.

NMR (DMSO-d₆)δ: 0.87 (3H, t), 1.14 (3H, t), 4.41 (1H, s)

Example 14

(1) Methyl 2-n-butyl-3-{2'-(1H-tetrazol-5-yl)-biphenyl-4-yl}methyl-4,5,6,7-tetrahydroimidazo[4,5-c]-pyridine-4-carboxylate and (4-chlorophenyl)acetic acid are treated in the same manner as in Example 8-(1) to give methyl 2-n-butyl 5 (4-chlorophenyl)acetyl-3-{2'-(1H-tetrazol-5-yl)biphenyl-4-yl]methyl-4,5,6,7-tetrahydroimidazo[4,5-c]pyridine-4-carboxylate.

NMR (CDCl₃)δ: 0.97 (3H, t), 3.75 (3H, s), 3.78 (2H, s)

(2) To a mixture of the above product (304 mg) and t-butanol (10 ml) is added potassium t-butoxide (120 mg), and the mixture is stirred at room temperature for 40 minutes. The mixture is evaporated under reduced pressure to remove the solvent, and the resulting residue is acidified with hydrochloric acid. The mixture is extracted with a mixture of chloroform and methanol, and the extract is washed, dried and evaporated under reduced pressure to remove the solvent. The resulting residue is purified by silica gel column chromatography (solvent; chloroform/methanol) to give 2-n-butyl-8-(4-chlorophenyl)-9-hydroxy-1-{2'-(1H-tetrazol-5-yl)biphenyl-4-yl}methyl-1,4,5,9a-tetrahydro-7H imidazo[4,5-g]indolizin-7-one (131 mg) as powder.

NMR (DMSO-d₆)δ: 0.80 (3H, t), 4.54 (1H, s)

(3) To a mixture of the above product (165 mg) and methanol (20 ml) is added 1N aqueous sodium hydroxide solution (0.56 ml). The mixture is evaporated under reduced pressure to remove the solvent, and the resulting residue is purified by column chromatography of nonionic adsorbing resin (tradename; HP-20, manufactured by Mitsubishi Kasei Corporation), and lyophilized to give 2-n-butyl-8-(4-chlorophenyl)-9-hydroxy-1-{2-(1H-tetrazol-5-yl)biphenyl-4-yl}methyl-1,4,5,9a-tetrahydro-7H-imidazo[4,5-g]indolizin-7-one disodium salt (99 mg) as powder.

NMR (D₂O)δ: 0.77 (3H, t), 4.63 (1H, s)

Example 15

(1) Ethyl 2-n-butyl-3-(2'-methoxycarbonylbiphenyl-4-yl)methyl-4,5,6,7-tetrahydroimidazo[4,5-c]pyridine-4-carboxylate and ethoxycarbonylacetic acid are treated in the same manner as in Example 8-(1) to give ethyl 2-n-butyl-5-ethoxycarbonylacetyl-3-(2'-methoxycarbonylbiphenyl-4-yl)-methyl-4,5,6,7-tetrahydroimidazo[4,5-c]pyridine-4-carboxylate.

NMR (CDCl₃)δ: 0.84–0.96 (3H, m), 3.57 (2H, s)

(2) To a mixture of the above product (409 mg) and ethanol (4 ml) is added a mixture of sodium hydride (62% oil-dispersion type) (30 mg) and ethanol (4 ml), and the mixture is stirred at room temperature for 10 minutes, evaporated under reduced pressure to remove the solvent, and to the resulting residue is added saturated aqueous ammonium chloride solution, and the mixture is extracted with chloroform. The extract is dried, and evaporated under reduced pressure to give 2-n-butyl-8-ethoxycarbonyl-9-hydroxy-1-(2'-methoxycarbonylbiphenyl-4-yl)methyl-1,4,5,9a-tetrahydro-7H-imidazo[4,5-g]indolizin-7-one (372 mg) as foam.

(3) The above product is treated in the same manner as in Example 14-(3) to give 2-n-butyl-8-ethoxycarbonyl-9-hydroxy-1-(2'-carboxybiphenyl-4-yl)methyl-1,4,5,9a-tetrahydro-7H-imidazo[4,5-g]indolizin-7-one disodium salt as powder.

NMR (D₂O)δ: 0.82 (3H, t), 1.27 (3H, t), 4.76 (1H, s)

Example 16

(1) To a mixture of ethyl 2-n-propyl-3-{2'-(1H-tetrazol-5-yl)biphenyl-4-yl}methyl-4,5,6,7-tetrahydroimidazo[4,5-c]pyridine-4-carboxylate (1.00 g), cyanoacetic acid (0.36 g) and methylene chloride (20 ml) is added 1-ethyl-3-(3-dimethylaminopropyl)carbodiimide hydrochloride (0.82 g) at room temperature. The reaction mixture is stirred overnight at room temperature, and then washed with 2% aqueous hydrochloric acid and brine. The organic layer is dried and evaporated to remove the solvent. The crude residue is purified by silica gel column chromatography (solvent; chloroform/methanol) to give ethyl 2-n-propyl-3-{2'-(1H-tetrazol-5-yl)biphenyl-4-yl}methyl-5-cyanoacetyl-4,5,6,7-tetrahydroimidazo[4,5-c]pyridine-4-carboxylate (0.76 g) as white foam.

FAB-MS (m/z): 539 (MH⁺), 207 (base)

(2) The above product is treated in the same manner as in Example 5-(2) to give 2-n-propyl 8-cyano-9-hydroxy-1-{2'-[1H-tetrazol-5-yl)biphenyl-4-yl}methyl-1,4,5,9a-tetrahydro-7H-imidazo[4,5-g]indolizin-7-one disodium salt.

NMR (D$_2$O)δ: 0.80 (3H, t), 4.51 (1H, s), 5.22 (1H, d), 5.90 (1H, d)

Example 17

(1) Ethyl 2-n-propyl-3-(2'-(1H-tetrazol-5-yl)-biphenyl-4-yl}methyl-4,5,6,7-tetrahydroimidazo[4,5-c]-pyridine-4-carboxylate is treated in the same manner as in Example 12-(1) to give ethyl 2-n-propyl-5-acetoacetyl-3-{2'-(1H-tetrazol-5-yl)biphenyl-4-yl}methyl-4,5,6,7-tetrahydroimidazo[4,5-c]pyridine-4-carboxylate as white foam.

NMR (CDCl$_3$)δ: 1.03 (3H, t), 2.22 (3H, s), 3.61 (2H, ABq), 5.30 (2H, ABq), 5.36 (1H, s)

(2) The above product is treated in the same manner as in Example 5-(2) to give 2-n-propyl-8-acetyl-9-hydroxy-1-{2'-(1H-tetrazol-5-yl)biphenyl-4-yl}methyl-1,4,5,9a-tetrahydro-7H-imidazo[4,5-g]indolizin-7-one disodium salt.

NMR (D$_2$O)δ: 0.80 (3H, t), 4.38 (1H, brs), 5.24 (1H, d), 6.03 (1H, d)

Example 18

(1) To a mixture of ethyl 2-n-propyl-5-aceto-acetyl-3-{2'-(1H-tetrazol-5-yl)biphenyl-4-yl}methyl-4,5,6,7-tetrahydroimidazo[4,5-c]pyridine-4-carboxylate (200 mg), magnesium chloride (34 mg), pyridine (58 μl) and acetonitrile (2 ml) is added benzoyl chloride (42 μl) under ice-cooling. The reaction mixture is stirred overnight at room temperature and diluted with chloroform (50 ml). The solution is washed with 10% hydrochloric acid and brine, dried, and evaporated to remove the solvent to give crude residue (266 mg) as oil. The residue (260 mg) obtained above is refluxed with 10% hydrochloric acid (1.0 ml) in ethanol (5.0 ml) for one hour. The reaction mixture is diluted with chloroform (30 ml), washed with brine, dried, and then evaporated to remove the solvent. The resulting residue is purified by silica gel column chromatography (solvent; chloroform/ethanol) to give ethyl 2-n-propyl-5-benzoylacetyl-3-{2'-(1H-tetrazol-5-yl)biphenyl}methyl-4,5,6,7-tetrahydroimidazo[4,5-c]pyridine-4-carboxylate (144 mg) as white foam.

FAB-MS (m/z): 618 (MH+), 207 (base)

NMR (CDCl$_3$)δ: 1.04 (3H, t), 4.00–4.28 (5H, m), 5.30 (2H, s), 5.40 (1H, s)

(2) The above product is treated in the same manner as in Example 5-(2) to give 2-n-propyl-8-benzoyl-9-hydroxy-1-{2'-(1H-tetrazol-5-yl)biphenyl-4-yl}methyl-1,4,5,9a-tetrahydro-7H-imidazo[4,5-g]indolizin-7-one disodium salt as white powder.

FAB-MS (m/z): 616 (MH+), 119 (base)

NMR (D$_2$O)δ: 0.80 (3H, t), 4.57 (1H, s), 5.24 (1H, d), 5.90 (1H, d)

Example 19

(1) Ethyl 2-n-propyl-3-{2'-(tert-butoxycarbonyl)-biphenyl-4-yl}methyl-4,5,6,7-tetrahydroimidazo[4,5-c]-pyridine 4-carboxylate oxalate (1.00 g) is suspended in chloroform. The suspension is washed with saturated sodium hydrogen carbonate solution and brine, dried over magnesium sulfate, and evaporated to remove the solvent. To a mixture of the crude substrate (0.75 g), ethoxycarbonylacetic acid (0.33 g) and methylene chloride (10 ml) is added 1-ethyl-3-(3-dimethylaminopropyl)carbodiimide hydrochloride (0.48 g) at room temperature. The reaction mixture is stirred for one hour and washed with 10% aqueous citric acid solution, saturated sodium hydrogen carbonate solution and brine. The organic layer is dried and evaporated to remove the solvent. The resulting crude residue is purified by silica gel column chromatography (solvent; chloroform/ethyl acetate) to give ethyl 2-n-propyl-3-{2'-(tert-butoxy-carbonyl)biphenyl-4-yl}methyl-5-ethoxycarbonylacetyl-4,5,6,7-tetrahydroimidazo[4,5-c]pyridine-4-carboxylate (0.70 g).

FAB-MS (m/z): 618 (MH+), 211 (base)

NMR (CDCl$_3$)δ: 1.12 (3H, t), 1.28 (9H, s), 3.57 (2H, s), 5.37 (2H, ABq)

(2) The mixture of ethyl 2-n-propyl-3-{2'-(tert-butoxycarbonyl)biphenyl-4-yl}methyl-5-ethoxycarbonylacetyl-4,5,6,7-tetrahydroimidazo[4,5-c]pyridine-4-carboxylate (657 mg), trifluoroacetic acid (3 ml) and methylene chloride (10 ml) is stirred overnight at room temperature. The reaction mixture is washed with saturated sodium hydrogen carbonate solution and brine, dried and evaporated to remove the solvent. The crude residue is purified by silica gel column chromatography (solvent; chloroform/methanol) to give ethyl 2-n-propyl-3-(2 -carboxybiphenyl-4-yl)methyl-5-ethoxycarbonylacetyl-4,5,6,7-tetrahydroimidazo[4,5-c]pyridine-4-carboxylate (516 mg).

FAB-MS (m/z): 562 (MH+), 211 (base)

NMR (CDCl$_3$)δ: 0.76 (3H, t), 3.55 (2H, s), 5.34 (2H, ABq)

(3) The above product is treated in the same manner as in Example 5-(2) to give 2-n-propyl-8-ethoxycarbonyl-9-hydroxy-1-{2'-carboxybiphenyl-4-yl)methyl-1,4,5,9a-tetrahydro-7H-imidazo[4,5-g]indolizin-7-one disodium salt.

FAB-MS (m/z): 582 (M+Na), 560 (MH+), 177 (base)

NMR (D$_2$O)δ: 0.86 (3H, t), 5.38 (1H, d), 6.25 (1H, d)

Example 20

(1) Ethyl 2-ethyl-3-{2'-(1-trityl-1H-tetrazol-5-yl)biphenyl-4-yl}methyl-4,5,6,7-tetrahydroimidazo[4,5-c]-pyridine-4-carboxylate (1.94 g), monoethyl malonate (0.74 g), 1-ethyl-3-(3-dimethylaminopropyl)carbodiimide hydrochloride (0.80 g), and triethylamine (1.40 g) are dissolved in dichloromethane (20 ml). The mixture is stirred overnight at room temperature. The reaction mixture is washed with water, dried over sodium sulfate, and then evaporated to remove the solvent. The residue is dissolved in ethanol (30 ml) and thereto is added fumaric acid (2.00 g). The mixture is refluxed for three hours and evaporated to remove the solvent. The resulting residue is treated with a saturated sodium hydrogen carbonate solution and extracted with chloroform. The organic layer is dried and evaporated to remove the solvent. The resulting residue is purified by silica gel column chromatography (solvent; chloroform/methanol) to give ethyl 2-ethyl-3-{2'-(1H-tetrazol-5-yl)biphenyl-4-yl}methyl-5-ethoxycarbonylacetyl-4,5,6,7-tetrahydroimidazo[4,5-c]pyridine-4-carboxylate (1.07 g) as foam.

NMR (CDCl$_3$)δ: 5.29 (2H, s), 5.48 (1H, s), 6.92 (2H, d), 7.10 (2H, d)

(2) The above product is treated in the same manner as in Example 5-(2) to give 2-ethyl-8-ethoxycarbonyl-9-hydroxy-1-[2'-(1H-tetrazol-5-yl)biphenyl-4-yl}methyl- 1,4,5,9a-tetrahydro-7H-imidazo[4,5-g]indolizin-7-one disodium salt as white powder.

NMR (DMSO-d₆)δ: 1.10 (3H, t), 1.15 (3H, t), 4.45 (1H, s), 5.05 (1H, d), 6.45 (1H, d)

Example 21

(1) Ethyl 2-ethyl-3-{2'-(t-butoxycarbonyl)-biphenyl-4 yl}methyl-4,5,6,7-tetrahydroimidazo[4,5-c]-pyridine-4-carboxylate is treated in the same manner as in Example 20-(1) to give ethyl 2-ethyl-3-{2'-(t-butoxycarbonyl)-biphenyl-4-yl}methyl 5-ethoxycarbonylacetyl-4,5,6,7-tetrahydroimidazo[4,5-c]pyridine-4-carboxylate as oil.

NMR (CDCl₃)δ: 1.12 (3H, t), 1.28 (9H, s), 5.35 (2H, q), 6.00 (1H, s)

(2) The above product is treated in the same manner as in Example 19-(2) to give ethyl 2-ethyl-3-{2'-carboxybiphenyl-4-yl)methyl-5-ethoxycarbonylacetyl-4,5,6,7-tetrahydroimidazo[4,5-c]pyridine-4-carboxylate as white foam.

NMR (CDCl₃)δ: 0.98 (3H, t), 1.16 (3H, t), 1.27 (3H, t), 5.33 (2H, q), 6.00 (1H, s)

(3) The above product is treated in the same manner as in Example 5-(2) to give 2-ethyl-8-ethoxycarbonyl-9-hydroxy-1-{2'-carboxybiphenyl-4-yl)methyl-1,4,5,9a-tetrahydro-7H-imidazo[4,5-g]indolizin-7-one disodium salt as white foam.

NMR (DMSO-d₆)δ: 4.50 (1H, s), 5.17 (1H, d), 6.36 (1H, d)

Reference Example 1

(1) 2-n-Butyl-4-hydroxymethylimidazole (33.3 g) is dissolved in methanol (50 ml), and thereto is added 18% hydrogen chloride-methanol solution (160 ml), and the mixture is evaporated under reduced pressure to remove the solvent. To the resulting residue is added toluene (150 ml), and thereto is added dropwise thionyl chloride (52 ml) under ice-cooling. The mixture is stirred at 50° C. for two hours, and concentrated to dryness under reduced pressure to give 2-n-butyl-4-chloromethylimidazole hydrochloride (58.3 g) as oil. Separately, diethyl N-acetylaminomalonate (140.8 g) is added to a solution of sodium ethylate (44 g) in ethanol (500 ml) with ice-cooling under argon atmosphere, and the mixture is stirred at 0° C. for 15 minutes. To the mixture is added dropwise a solution of 2-n-butyl-4-chloromethylimidazole hydrochloride obtained above in ethanol (250 ml), and the mixture is stirred at room temperature overnight. The mixture is evaporated under reduced pressure to remove the solvent, and to the resulting residue are added ethyl acetate (1 liter) and saturated aqueous ammonium chloride solution (500 ml). The aqueous layer is extracted with ethyl acetate, and the extract is combined with the organic layer, and evaporated. To the resulting residue is added 10% hydrochloric acid, and the mixture is neutralized with sodium hydrogen carbonate, and extracted with ethyl acetate to give 2 n butyl-4-{2-acetylamino-2,2-bis(ethoxycarbonyl)ethyl}imidazole (56.8 g) as powder.

m.p. 80°-92° C.

NMR (CDCl₃); 0.91 (3H, t), 1.24 (6H, t), 2.01 (3H, s), (2) The above product is added to 6N hydrochloric acid (600 ml), and the mixture is refluxed overnight. The mixture is concentrated to dryness under reduced pressure, and the resulting residue is dissolved in methanol (200 m). The oily residue is subjected to azeotropic distillation with toluene to remove water to give 2-n-butyl-4-{2-amino-2-(methoxycarbonyl)ethyl}imidazole hydrochloride (46.0 g) as oil.

NMR (DMSO-d₆)δ: 0.96 (3H, t), 3.28 (2H, d), 3.73 (3H, s)

(3) The above product (45 g) is added to 37% aqueous formalin solution (45 ml) and water (600 ml), and the mixture is refluxed for two hours. The reaction solution is evaporated under reduced pressure, and the resulting crystalline residue is pulverized in acetone, and collected by filtration to give 2-n-butyl-4,5,6,7-tetrahydroimidazo[4,5-c]pyridine-6-carboxylic acid hydrochloride (50 g).

m.p. 176°-179° C. (decomposed)

(4) The above product (30 g) is suspended in methanol (300 ml), and thereto is added thionyl chloride (30 ml), and the mixture is refluxed overnight. The reaction solution is evaporated under reduced pressure to give methyl 2-n-butyl-4,5,6,7-tetrahydroimidazo[4,5-c]pyridine-6-carboxylate hydrochloride (28.3 g) as oil.

NMR (D20)δ: 0.90 (3H, t), 3.92 (3H, s)

(5) N-Hydroxysuccinimide (0.69 g) and triethylamine (0.6 g) are dissolved in dry dimethylformamide (5 ml), and thereto is added dropwise benzyloxycarbonyl chloride (1.02 g) under ice-cooling. The mixture is stirred for 10 minutes, and thereto is added triethylamine (2.0 g). To the mixture is further added a solution of methyl 2-n-butyl-4,5,6,7-tetrahydroimidazo[4,5-c]pyridine-6-carboxylate hydrochloride (1.55 g) in dimethylformamide (5 ml), and the mixture is stirred at room temperature overnight. The reaction solution is concentrated under reduced pressure, and thereto are added water and chloroform. The aqueous layer is extracted with chloroform, and the extract is combined with the chloroform layer, dried, and evaporated under reduced pressure to remove the solvent. The resulting oily residue is purified by silica gel column chromatography (solvent; chloroform/methanol) to give methyl 2-n-butyl-5-benzyloxycarbonyl-4,5,6,7-tetrahydroimidazo[4,5-c]pyridine-6-carboxylate (1.21 g) as pale yellow oil.

NMR (CDCl₃)δ: 0.90 (3H, t), 3.63 (3H, s), 5.20 (2H, s)

(6) The above product (12.69 g) is dissolved in dimethylformamide (300 ml), and thereto is added sodium hydride (60% oil-dispersion type) (1.83 g) under ice-cooling, and the mixture is stirred at 0° C. for three hours. To the mixture is added 2'-(1-trityl-1H-tetrazol-5-yl)biphenyl 4-ylmethyl bromide (23.81 g), and the mixture is stirred under ice-cooling for one hour, and further stirred at room temperature for one hour. The reaction solution is concentrated under reduced pressure, and to the residue are added ethyl acetate and water. The organic layer is dried, and evaporated under reduced pressure to give yellow foam, which is further purified and separated by silica gel column chromatography. That is, firstly, methyl 2-n-butyl-5-benzyloxycarbonyl-1-{2'-(1-trityl-1H-tetrazol-5-yl)biphenyl-4yl}methyl-4,5,6,7-tetrahydroimidazo[4,5-c]pyridine-6-carboxylate (14.68 g) [hereinafter referred to as Product (A)] is obtained as foam from the fractions eluated with chloroform:ethyl acetate =3:1, and subsequently methyl 2-n-butyl-5-benzyloxycarbonyl-3-{2'-(1-trityl-1H-tetrazol-5-yl)biphenyl-4-yl}methyl-4,5,6,7-tetrahydroimidazo[4,5-c]pyridine-6-carboxylate (8.23 g) [hereinafter referred to as Product (B)] is obtained as foam from the fractions eluated with chloroform:ethyl acetate=2:1.

Product (A)

NMR (CDCl₃)δ: 0.86 (3H, t), 3.60 (3H, s)

Product (B)

NMR (CDCl$_3$)δ: 0.85 (3H, t), 3.58 and 3.63 (3H, each s) (each singlet comes to 3H in all)

Reference Example 2

(1) 1-t-Butoxycarbonyl-4-{2-(t-butoxycarbonyl-amino)ethyl}imidazole (78.1 g) is dissolved in acetonitrile (500 ml), and thereto is added methoxymethyl chloride (22.2 g), and the mixture is stirred at room temperature overnight. The reaction solution is poured into 10% aqueous sodium hydrogen carbonate solution, and extracted with ethyl acetate. The extract is washed, dried, and the solvent is distilled off to give 4-{2-(t-butoxycarbonyl-amino)ethyl]-3-methoxymethylimidazole (54.4 g) as oil.

NMR (CDCl$_3$)δ: 1.43 (9H, s), 3.27 (3H, s), 5.20 (2H, s).

(2) The above product (55 g) is dissolved in tetrahydrofuran (1.5 liter), and the mixture is cooled to −40° C. To the mixture is added dropwise 1.6M n-butyl lithium/n-hexane solution (150 ml), and the mixture is stirred for 30 minutes. To the mixture are added successively hexamethylphosphoamide (150 ml) and n-butyl lithium (137 ml), and further n-butyl iodide (37.5 g) is added dropwise to the mixture during which the mixture is kept at −30° C. After the mixture is stirred for 10 minutes, the reaction is quenched by adding aqueous ammonium chloride solution thereto. Ethyl acetate is added to the mixture, and the mixture is separated. The organic layer is collected, washed and dried, and the solvent is distilled off. The resulting oily residue is purified by silica gel column chromatography (solvent; chloroform/ethyl acetate/methanol) to give 2-n-butyl-4-{2-(t-butoxycarbonylamino)-ethyl]-3-methoxymethylimidazole (44.8 g) as oil.

NMR (CDCl$_3$)δ: 0.94 (3H, t), 1.44 (9H, s), 3.27 (3H, s), 5.09 (2H, s)

(3) Chloroform (1.3 liter) is added to the above product (80.7 g) and ethyl chloroformate (84.5 g), and the mixture is refluxed for 2.5 hours. The reaction solution is evaporated under reduced pressure, and to the resulting residue are added ethanol (300 ml) and 10% aqueous sodium hydroxide solution (200 ml), and the mixture is stirred under ice-cooling for 20 minutes. The solvent is distilled off, and to the residue are added water and chloroform, and the mixture is separated. The organic layer is dried, and the solvent is distilled off, and the resulting solid product is recrystallized from isopropyl ether to give 2-n-butyl-4-{2-(t-butoxycarbonylamino)ethyl}imidazole (50.3 g).

m.p. 118°–120° C.

(4) The above product and 2'-(1-trityl-1H-tetrazol-5-yl)biphenyl-4-ylmethyl bromide are treated in the same manner as in Reference Example 1-(6) to give 2-n-butyl-4-(2-(t-butoxycarbonylamino)ethyl]-1-{2'-(1-trityl-1H-tetrazol-5-yl)biphenyl-4-yl}methylimidazole.

NMR (CDCl$_3$)δ: 0.89 (3H, t), 1.43 (9H, s), 4.85 (2H, s)

(5) A mixture of the above product (15.2 g), 10% hydrochloric acid (40 ml) and methanol (60 ml) is refluxed for one hour. After the reaction is completed, methanol is removed by distillation, and the aqueous layer is washed with ethyl acetate and concentrated to dryness under reduced pressure. The resulting residue is subjected to azeotropic distillation with dry toluene to give quantatively crude 2-n-butyl-4-(2-aminoethyl)-1-{2'-(1H-tetrazol-5-yl)biphenyl-4-yl}methylimidazole hydrochloride (9.7 g) as caramel.

NMR (DMSO-d$_6$)δ: 0.84 (3H, t), 1.43 (9H, s), 5.40 (2H, s)

(6) A mixture of the above product (8.09 g), glyoxylic acid hydrate (1.73 g), 1N aqueous sodium hydroxide solution (53 ml) and dioxane (50 ml) is stirred at about 50° C. for 2 days. The reaction solution is acidified with hydrochloric acid, and evaporated under reduced pressure. The resulting residue is dissolved in methanol (100 ml), and cooled to −30° C., and thereto is added dropwise thionyl chloride (12.4 g). After the mixture is stirred at about 60° C. for 2 days, the solvent is distilled off under reduced pressure. Water is added to the resulting residue, and the mixture is neutralized with aqueous sodium hydrogen carbonate solution, and extracted with chloroform. The extract is dried and evaporated under reduced pressure, and the resulting oily product is purified by silica gel column chromatography (solvent; chloroform/methanol) to give methyl 2-n-butyl-3-{2'-(1H-tetrazol-5-yl)biphenyl-4-yl}methyl-4,5,6,7-tetrahydroimidazo[4,5-c]pyridine-4-carboxylate (4.22 g) as powder.

NMR (DMSO-d$_6$)δ: 0.90 (3H, t), 3.72 (3H, s), 5.20 (2H, s)

Reference Example 3

(1) 2-n-Propyl-4-hydroxymethylimidazole and diethyl N-acetylaminomalonate are treated in the same manner as in Reference Example 1-(1) to give 2-n-propyl-4-{2-acetylamino-2,2-bis(ethoxycarbonyl)ethyl}imidazole as powder.

m.p. 94°–97° C.

(2) The above product is treated in the same manner as in Reference Example 1-(2) to give 2-n-propyl-4-{2-amino-2-(methoxycarbonyl)ethyl}imidazole hydrochloride as oil.

NMR (DMSO-d$_6$)δ: 0.91 (3H, t), 3.28 (2H, d), 3.73 (3H, s)

(3) To a mixture of the above product (5.74 g), triethylamine (6.81 g) and chloroform (200 ml) is added dropwise a solution of benzyloxycarbonyl chloride (2.87 g) in chloroform (100 ml) under ice-cooling. The mixture is stirred at room temperature overnight, washed and dried, and the solvent is distilled off. The resulting residue is purified by silica gel column chromatography (solvent; chloroform/methanol) to give 2-n-propyl-4-{2-(N-benzyloxycarbonyl)amino-2-(methoxycarbonyl)ethyl}imidazole (3.36 g) as oil.

NMR (CDCl$_3$)δ: 0.92 (3H, t), 3.05 (2H, d), 3.67 (3H, s), 5.10 (2H, s)

(4) The above product and 2'-(1-trityl-1H-tetrazol-5-yl)biphenyl-4-ylmethyl bromide are treated in the same manner as in Reference Example 1-(6) except that the reaction is carried out overnight to give 2-n-propyl-1-{2'-(1-trityl-1H-tetrazol-5-yl)biphenyl-4-yl}methyl-4-(2-(N-benzyloxycarbonyl)amino-2-(methoxycarbonyl)ethyl]imidazole as foam.

NMR (CDCl$_3$)δ: 0.89 (3H, t), 3.63 (3H, s), 4.83 (2H, s), 5.11 (2H, s)

(5) To a mixture of the above product (5.18 g) and methanol (40 ml) is added 9% hydrogen chloride-methanol solution (60 ml), and the mixture is stirred at room temperature for one hour, and evaporated. The resulting residue is dissolved in methanol (50 ml), and the mixture is subjected to catalytic reduction by using 10% palladium-carbon as a catalyst. After the reaction is completed, the catalyst is removed by filtration, and the solvent is distilled off. The resulting oily residue is dissolved in methanol (50 ml), and the mixture is refluxed with aqueous formalin solution (4 ml) for one hour. After distillation of the solvent, the product is pulverized in ethyl acetate, and collected by filtration to give methyl 2-n-propyl-3-{2'-(1H-tetrazol-5-yl)biphenyl-4-yl}methyl-4,5,6,7-tetrahydroimidazo[4,5-c]pyridine-6-carboxylate hydrochloride (3.73 g) as powder.

NMR (CDCl$_3$)δ: 0.92 (3H, t), 3.71 (3H, s), 4.86 (2H, ABq)

Reference Example 4

(1) 2-n-Propyl-4-hydroxymethylimidazole (2.61 g) is added to thionyl chloride (4.5 ml), and the mixture is heated at 50° C. for two hours. The solvent is distilled off, and the resulting residue is dissolved in dimethylformamide (20 ml), and added dropwise to a solution of sodium cyanide (5.47 g) in dimethylformamide (120 ml). The mixture is stirred at room temperature overnight, and the solvent is distilled off. The resulting residue is dissolved in ethyl acetate, washed, dried and evaporated. The resulting residue is purified by silica gel column chromatography (solvent; ethyl acetate) to give 2-n-propyl-4-cyanomethylimidazole (3.08 g) as oil.

NMR (CDCl$_3$)δ: 0.95 (3H, t), 3.67 (2H, d)

(2) The above product (3.08 g) is dissolved in acetic acid (30 ml), and thereto is added 10% hydrochloric acid (10 ml). The mixture is subjected to catalytic reduction by using platinum oxide as a catalyst. After the reaction is completed, the catalyst is removed by filtration, and the filtrate is evaporated under reduced pressure to give 2-n-propyl-4-(2-aminoethyl)imidazole hydrochloride (4.83 g), which is used in a subsequent reaction without further purification.

(3) A mixture of the above product (4.83 g), phthalic anhydride (3.04 g), sodium acetate (6.10 g) and acetic acid (50 ml) is refluxed for 19 hours. The mixture is evaporated under reduced pressure, and to the residue is added water. The mixture is neutralized with sodium hydrogen carbonate, and extracted with chloroform. The extract is dried and the solvent is distilled off, and the resulting residue is purified by silica gel column chromatography (solvent; chloroform/methanol) to give 2-n-propyl-4-(2-phthalimidethyl)imidazole (2.72 g) as foam.

NMR (CDCl$_3$)δ: 0.90 (3H, t), 3.95 (2H, t), 7.61-7.86 (4H, m)

(4) The above product and 2'-(1-trityl-1H-tetrazol-5-yl)biphenyl-4-ylmethyl bromide are treated in the same manner as in Reference Example 1-(6) except that the reaction is carried out overnight to give 2-n-propyl-4-(2-phthalimidethyl)-1-{2'-(1-trityl-1H-tetrazol-5-yl)biphenyl-4-yl}methylimidazole as foam.

NMR (CDCl$_3$)δ: 0.86 (3H, t), 4.82 (2H, s)

(5) To a mixture of the above product (4.11 g) and ethanol (100 ml) is added 100% hydrazine hydrate (2 ml), and the mixture is stirred at room temperature for five hours. After the reaction is completed, chloroform is added to the reaction solution, and the mixture is washed, dried, and evaporated to give crude 2-n-propyl-4-(2-aminoethyl)-1-2'-(1 trityl-1H-tetrazol-5-yl)biphenyl-4-yl}methylimidazole (3.68 g) as oil.

(6) The above product is treated in the same manner as in Reference Example 2-(5) to give 2-n-propyl-4-(2-aminoethyl)-1-{2'-(1H-tetrazol-5-yl)biphenyl-4-yl}methylimidazole hydrochloride.

(7) The above product and glyoxylic acid hydrate are treated in the same manner as in Reference Example 2-(6) to give methyl 2-n-propyl-3-[2'-(1H-tetrazol-5-yl)biphenyl-4 yl}methyl-4,5,6,7-tetrahydroimidazo[4,5-c]pyridine-4-carboxylate as foam.

NMR (DMSO-d$_6$)δ: 0.98 (3H, t), 3.84 (3H, s), 5.06 (2H, ABq)

Reference Example 5

(1) 2-n-Butyl-4-{2-(t-butoxycarbonylamino)ethyl}-imidazole and 2'-(methoxycarbonyl)biphenyl-4-ylmethyl bromide are treated in the same manner as in Reference Example 1-(6) except that the reaction is carried out overnight to give 2-n-butyl-4-{2-(t-butoxycarbonylamino)-ethyl}-1-{2'-(methoxycarbonyl)-biphenyl-4-yl}methylimidazole.

NMR (CDCl$_3$)δ: 0.91 (3H, t), 3.66 (3H, s), 5.02 (2H, s)

(2) The above product is treated in the same manner as in Reference Example 2-(5) to give crude 2-n-butyl-4-(2-aminoethyl)-1-{2'-(methoxycarbonyl)biphenyl-4-yl}methylimidazole hydrochloride, which is further treated with glyoxylic acid hydrate in the same manner as in Reference Example 2-(6) to give crude methyl 2-n-butyl-3-{2'-(methoxycarbonyl)biphenyl-4-yl}methyl-4,5,6,7-tetrahydroimidazo[4,5-c]pyridine-4-carboxylate.

Reference Example 6

(1) To a mixture of 2-n-propyl-4-(2-aminoethyl)-1-{2'-(1-trityl-1H-tetrazol-5-yl)biphenyl-4-yl}methylimidazole (21.95 g) and tetrahydrofuran (200 ml) is added a solution of ethyl glyoxylate hydrate (4.25 g) in tetrahydrofuran (20 ml) at 5° C. The mixture is stirred overnight at room temperature and refluxed for 30 minutes. To a mixture is added a 8% hydrogen chloride-ethanol solution (100 ml) at room temperature. The reaction mixture is stirred for 30 minutes, and evaporated to remove the solvent. The residue is dissolved in chloroform and washed successively with saturated sodium hydrogen carbonate solution and brine. The organic layer is dried and evaporated to remove the solvent. The crude residue is treated with a mixture of oxalic acid and ethanol to give ethyl 2-n-propyl-3-{2'-(1H-tetrazol-5-yl)biphenyl-4-yl}methyl-4,5,6,7-tetrahydroimidazo[4,5-c]pyridine-4-carboxylate oxalate (10.84 g).

m.p. 140°-142° C.

(2) A suspension of the above product (4.0 g) in chloroform (300 ml) is washed with saturated sodium hydrogen carbonate solution and brine. The organic layer is dried and evaporated to remove the solvent to give ethyl 2-n-propyl-3-(2 -(1H-tetrazol-5-yl)biphenyl-4-yl}methyl-4,5,6,7-tetrahydroimidazo[4,5-c]pyridine-4-carboxylate (3.69 g) as white foam.

NMR (CDCl$_3$)δ: 1.00 (3H, t), 3.98 (1H, s), 5.09 (2H, q)

Reference Example 7

(1) To a mixture of 2-n-propyl-4-(2-phthalimidethyl)imidazole (10.0 g), 2'-t-butoxycarbonylbiphenyl-4-ylmethyl bromide (13.5 g), tetrahydrofuran (150 ml) and dimethylformamide (15 ml) is added a solution of potassium t-butoxide (4.16 g) in tetrahydrofuran (40 ml) at −60° C. After removing the cooling bath, the reaction mixture is stirred for 2.5 hours until the temperature thereof becomes room temperature. The mixture is quenched with water, and extracted with ethyl acetate. The organic layer is washed, dried and evaporated to remove the solvent. The crude residue is treated with a mixture of oxalic acid, ethanol and ether to give 2-n-propyl-4-(2-phthalimidethyl)-1-{2'-(t-butoxycarbonyl)-biphenyl-4-yl}methylimidazole oxalate (15.6 g).

m.p. 128°–131° C.

(2) The above product is treated in the same manner as in Reference Example 4-(5) except that the reaction is carried out overnight to give crude 2-n-propyl-4-aminoethyl-1-{2'-(tert-butoxycarbonyl)biphenyl-4-yl}-methylimidazole.

(3) To a mixture of the above product (10.0 g) and tetrahydrofuran (100 ml) is added a solution of ethyl glyoxylate hydrate (2.90 g) in tetrahydrofuran at room temperature. The reaction mixture is stirred overnight, refluxed for 30 minutes and evaporated to remove the solvent. The residue is dissolved in chloroform and the solution is washed with 2% hydrochloric acid, saturated aqueous sodium hydrogen carbonate solution and brine. The organic layer is dried and evaporated to remove the solvent. The crude residue is treated with a mixture of oxalic acid, ethanol and ether to give ethyl 2-n-propyl-3-{2'-(tert-butoxycarbonyl)biphenyl-4-yl}methyl-4,5,6,7-tetrahydroimidazo[4,5-c]pyridine-4-carboxylate oxalate.

m.p. 166°–168° C.

Reference Example 8

(1) To a stirred solution of 2-ethylimidazole (100 g) and triethylamine (115 g) in chloroform (800 ml) at 0° C. is added a solution of dimethylsulfamoyl chloride (153 g) in chloroform (200 ml). The mixture is stirred overnight at room temperature. Water (1.5 liter) is added thereto and the organic layer is separated therefrom and concentrated. The residue is dissolved in ethyl acetate (1 liter) and washed with water. The solution is dried over sodium sulfate and concentrated. Distillation gives 1-dimethylsulfamoyl-2-ethylimidazole (182 g) as colorless liquid.

b.p. 139°–142° C. (5 mmHg)

NMR (CDCl$_3$)$\delta$: 1.37 (3H, t), 2.89 (6H, s), 6.94 (1H, d), 7.23 (1H, d)

(2) To a stirred solution of the above product (53 g) in tetrahydrofuran (1 liter) at −78° C. is added 1.6M solution of n butyl lithium in hexane (185 ml). The solution is stirred at −78° C. for one hour, and then, N-t-butoxycarbonyl aziridine (52 g) in tetrahydrofuran (300 ml) is added thereto, and further boron trifluoride etherate (147 g) is added thereto successively. The reaction mixture is stirred for two hours at −78° C. and then the mixture is poured into an ice-cooled saturated aqueous potassium carbonate solution (2 liters). After evaporation of the remaining tetrahydrofuran, the aqueous layer is extracted with ethyl acetate, and the organic layer is washed with water, and dried over sodium sulfate and concentrated. The residue is purified by silica gel column chromatography (solvent; chloroform/methanol) to give 1-dimethylsulfamoyl-2-ethyl 5-{2-(t-butoxycarbonylamino)ethyl}imidazole (67 g) as yellow oil.

NMR (CDCl$_3$)$\delta$: 1.35 (3H, t), 1.43 (9H, s), 2.87 (6H, s), 6.72 (1H, s)

(3) A solution of the above product (67 g) in 10% hydrochloric acid (600 ml) is refluxed for two hours. The solvent is distilled off under reduced pressure and the resulting oily black residue is dissolved in acetic acid (300 ml). After addition of a mixture of sodium acetate (62 g) and phthalic anhydride (34 g), the reaction mixture is treated in the same manner as in Reference Example 4-(3) to give crude 2-ethyl 4-(2-phthalimidethyl)imidazole (26 g) as white powder.

(4) The above product and 2'-(1-trityl-1H-tetrazol-5-yl)biphenyl-4-ylmethyl bromide are treated in the same manner as in Reference Example 7-(1) and the resulting residue is purified by silica gel column chromatography (solvent; hexane/ethyl acetate) to give 2-ethyl-4-(2-phthalimidethyl)-1-{2'-(1-trityl-1H-tetrazol-5 yl)bipenyl-4-yl}methylimidazole as white foam, characterized as its fumaric acid salt.

m.p. 173°–174° C.

(5) The above product is treated in the same manner as in Reference Example 4-(5) except that the reaction is carried out overnight to give the crude 2-ethyl-4-aminoethyl-1-[2'-(1-trityl-1H-tetrazol-5-yl)biphenyl-4-yl}methylimidazole as foam.

(6) The above product (7.48 g) is dissolved in tetrahydrofuran (60 ml), to which is added ethyl glyoxylate hydrate (1.56 g). The reaction mixture is stirred overnight at room temperature and refluxed for one hour. The solvent is evaporated and the residue is purified by silica gel column chromatography (solvent; chloroform/methanol) to give ethyl 2-ethyl-3-{2'-(1-trityl-1H-tetrazol-5-yl)biphenyl-4-yl}methyl-4,5,6,7-tetrahydroimidazo[4,5-c]pyridine-4-carboxylate as foam, chracterized as its oxalic acid salt.

m.p. 142°–146° C.

Reference Example 9

(1) 2-Ethyl-4-(2-phthalimidethyl)imidazole and 2'-t-butoxycarbonylbiphenyl-4-ylmethyl bromide are treated in the same manner as Reference Example 8-(4) to give 2-ethyl-4-(2-phthalimidethyl)-1-{2'-(t-butoxycarbonyl)biphenyl-4-yl}methylimidazole as oil.

NMR (CDCl$_3$)$\delta$: 1.20 (3H, t), 1.25 (9H, s), 5.02 (2H, s), 6.64 (1H, s)

(2) The above product is treated in the same manner as in Reference Example 4-(5) except that the reaction is carried out overnight to give the crude 2-ethyl-4-aminoethyl-1-{2'-(t-butoxycarbonyl)biphenyl-4-yl}methylimidazole as oil.

(3) The above product is treated in the same manner as in Reference Example 7-(3) to give ethyl 2-ethyl-3-{2'-(t-butoxycarbonyl)biphenyl-4-yl}methyl-4,5,6,7-tetrahydroimidazo[4,5-c]pyridine-4-carboxylate as yellow oil.

NMR (CDCl$_3$)$\delta$: 1.22 (3H, t), 1.28 (9H, s), 1.31 (3H, t), 4.36 (1H, s)

FAB-MS (m/z): 490 (MH$^+$), 211 (base)

Effects of the invention

The imidazoindolizine derivatives [I] of the present invention and pharmaceutically acceptable salts thereof show excellent angiotensin II antagonistic activities, and are useful in the prophylaxis and/or treatment of hypertension. For example, when hypotensive activity was examined by using spontaneously hypertensive rats orally administered at a dose of 3 mg/kg of the desired compounds [I] of the present invention, significant hypotensive activity was observed as compared with that of the control group of rats to which purified water was orally administered. Moreover, the compounds [I] of the present invention and pharmaceutically acceptable salts thereof show low toxicity, and hence, they show high safety as a medicament. For example, when 2-n-butyl-8-ethoxycarbonyl-9-hydroxy-1-{2 -(1H-tetrazol-5-yl)biphenyl-4-yl}methyl-1,4,5,9a-tetrahydro-7H imidazo[4,5-g]indolizin-7-one disodium salt was orally administered to mice at a dose of 300 mg/kg, no mouse died one week after the administration thereof.

What is claimed is:

1. An imidazoindolizine derivative of the formula [I]:

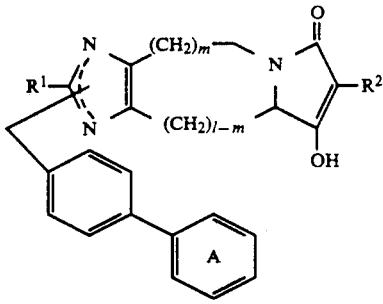

[I]

wherein R¹ is a lower alkyl group; R² is hydrogen atom; cyano group; a lower alkyl group; a lower alkanoyl group; a lower alkoxycarbonyl group; a phenyl-lower alkoxycarbonyl group; a lower alkylsulfonyl group; a phenyl group which is unsubstituted or substituted with a member selected from the group consisting of a halogen atom, a hydroxy group, a carboxyl group, a lower alkyl group, a lower alkoxy group, a lower alkoxy-carbonyl group and a carbamoyl group, or an arylcarbonyl group; Ring A is a phenyl group which is unsubstituted or substituted with a member selected from the group consisting of a tetrazolyl group, a trityl group-substituted tetrazolyl group, a carboxyl group, a lower alkyl group-substituted carboxyl group and a lower alkylsulfonylamino group; and m is 0 or 1, or a pharmaceutically acceptable salt thereof.

2. The compound according to claim 1, wherein R² is cyano group, a lower alkanoyl group, a lower alkoxycarbonyl group, a phenyl-lower alkoxycarbonyl group, a halogenophenyl group or benzoyl group, and Ring A is tetrazolylphenyl group or carboxyphenyl group.

3. The compound according to claim 2, wherein R¹ is ethyl group, n-propyl group or n-butyl group, R² is cyano group, acetyl group, methoxycarbonyl group, ethoxycarbonyl group, benzyloxycarbonyl group, chlorophenyl group or benzoyl group.

4. The compound according to claim 1, which is 2-n-butyl-7-ethoxycarbonyl-8-hydroxy-1-{2'-(1H-tetrazol-5-yl)biphenyl-4-yl}methyl-1,4,8a,9-tetrahydro-6H-imidazo(4,5-f)indolizin-6-one or a pharmaceutically acceptable salt thereof.

5. The compound according to claim 1, which is 2-n-butyl-7-cyano-8-hydroxy-1-{2'(1H-tetrazol-5-yl)biphenyl-4-yl}methyl-1,4,8a,9-tetrahydro-6H-imidazo(4,5-f)indolizin-6-one or a pharmaceutically acceptable salt thereof.

6. The compound according to claim 1, which is 2-n-butyl-7-methoxycarbonyl-8-hydroxy-3-{2'-(1H-tetrazol-5-yl)biphenyl-4-yl}-methyl-1,4,8a,9-tetrahydro-6H-imidazo(4,5-f)indolizin-6-one or a pharmaceutically acceptable salt thereof.

7. The compound according to claim 1, which is 2-n-butyl-7-ethoxy-carbonyl-8-hydroxy-3-{2'(1H-tetrazol-5-yl)biphenyl-4-yl)-methyl-1,4,8a,9-tetrahydro-6H-imidazo(4,5-f)indolizin-6-one or a pharmaceutically acceptable salt thereof.

8. The compound according to claim 1, which is 2-n-butyl-8-ethoxycarbonyl-9-hydroxy-1-{2'(1H-tetrazol-5-yl)biphenyl-4-yl)-methyl-1,4,5, 9a -tetrahydro-7H-imidazo(4,5-g)indolizin-7-one or a pharmaceutically acceptable salt thereof.

9. The compound according to claim 1, which is (−)-2-n-butyl-8-ethoxycarbonyl-9-hydroxy-1-{2'-(1H-tetrazol-5-yl)biphenyl-4-yl}methyl-1,4,5,9a-tetrahydro-7H-imidazo(4,5-g)indolizin-7-one or a pharmaceutically acceptable salt thereof.

10. The compound according to claim 1, which is (+)-2-n-butyl-8-ethoxycarbonyl-9-hydroxy-1-{2'-(1H-tetrazol-5-yl)biphenyl-4-yl}-methyl-1,4,5,9a-tetrahydro-7H-imidazo(4,5-g)indolizin-7-one or a pharmaceutically acceptable salt thereof.

11. The compound according to claim 1, which is 2-n-propyl-7-ethoxycarbonyl-8-hydroxy-3-{2'-(1h-tetrazol-5-yl)biphenyl-4-yl}-methyl-1,4,8a,9-tetrahydroimidazo(4,5-f)indolizin-6-one or a pharmaceutically acceptable salt thereof.

12. The compound according to claim 1, which is 2-n-butyl-7cyano-8-hydroxy-3-{2'-(1H-tetrazol-5-yl)biphenyl-4-yl}methyl-1,4,8a,9-tetrahydroimidazo(4,5-f)indolizin-6-one or a pharmacetucially acceptable salt thereof.

13. The compound according to claim 1, which is 2-n-butyl-7-benzyloxycarbonyl-8-hydroxy-3-{2'-(1H-tetrazol-5-yl)biphenyl-4-yl}-methyl-1,4,8a,9-tetrahydroimidazo(4,5-f)indolizin-6-one or a pharmaceutically acceptable salt thereof.

14. The compound according to claim 1, which is 2-n-butyl-8-cyano-9-hydroxy-1-{2'-(1H-tetrazol-5-yl)biphenyl-4-yl}methyl-1,4,5,9a-tetrahydro-7H-imidazo(4,5-g)indolizin-7-one or a pharmaceutically acceptable salt thereof.

15. The compound according to claim 1, which is 2-n-butyl-8-acetyl-9-hydroxy-1-{2'-(1H-tetrazol-5-yl)biphenyl-4-yl}methyl-1,4,5,9a-tetrahydro-7H-imidazo(4,5-g)indolizin-7-one or a pharmacetucially acceptable salt thereof.

16. The compound according to claim 1, which is 2-n-propyl-8-ethoxycarbonyl-9-hydroxy-1-{2'-(1H-tetrazol-5-yl)biphenyl-4-yl}-methyl-1,4,5,9a-tetrahydro-7Himidazo(4,5-g)indolizin-7-one or a pharmaceutically acceptable salt thereof.

17. The compound according to claim 1, which is 2-n-butyl-8-(4-chlorophenyl)-9-hydroxy-1-{2'-(1H-tetrazol-5-yl)biphenyl-4-yl}-methyl-1,4,5,9a-tetrahydro-7H-imidazo(4,5-g)indolizin-7-oneor a pharmaceutically acceptable salt thereof.

18. The compound according to claim 1, which is 2-n-butyl-8-ethoxycarbonyl-9-hydroxy-1-(2'carboxybiphenyl-4-yl)methyl-1,4,5,9a-tetrahydro-7Himidazo(4,5-g)indolizin-7-one or a pharmaceutically acceptable salt thereof.

19. The compound according to claim 1, which is 2-n-prpyl-8-cyano-96hydroxy-1-{2'-(1H-tetrazol-5-yl)biphenyl-4-yl}methyl-1,4,5,9a-tetrahydro-7H-imidazo(4,5-g)indolizin-7-one or a pharmaceutically acceptable salt thereof.

20. The compound according to claim 1, which is 2-n-propyl-8-acetyl-9-hydroxy-1-{2'-(1H-tetrazol-5-yl)biphenyl-4-yl}methyl-1,4,5,9a-tetrahydro-7H-imidazo(4,5-g)indolizin-7-one or a pharmaceutically acceptable salt thereof.

21. The compound according to claim 1, which is 2-n-propyl-8-benzoyl-9-hydroxy-1-{2'-(1H-tetrazol-5-yl)biphenyl-4-yl}methyl-1,4,5,9a-tetrahydro-7H-imidazo(4,5-g)indolizin-7-one or a pharmaceutically acceptable salt thereof.

22. The compound according to claim 1, which is 2-n-propyl-8-ethoxycarbonyl-9-hydroxy-1-(2'-carboxybiphenyl-4yl)methyl-1,4,5,9a-tetrahydro-7H-imidazo(4,5-g)indolizin-7-one or a pharmaceutically acceptable salt thereof.

23. The compound according to claim 1, which is 2-ethyl-8-ethoxycarbonyl-9-hydroxy-1-{2'-(1H-tetrazol-5-yl)biphenyl-4-yl}methyl-1,4,5,9a-tetrahydro-7H-imidazo(4,5-g)indolizin-7-one or a pharmaceutically acceptable salt thereof.

24. The compound according to claim 1, which is 2-ethyl-8-ethoxycarbonyl-9-hydroxy-1-(2'-carboxybiphenyl-4-yl)methyl-1,4,5,9a-tetrahydro-7H-imidazo(4,5-g)indolizin-7-one or a pharmaceutically acceptable salt thereof.

25. A pharmaceutical composition which comprises a therapeutically effecitve amount of the compound as set forth in claim 1 in admixture with a conventional pharmaceutically acceptable carrier or diluent.

26. A method for the prophylaxis or treatment of hypertension which comprises administering to a warm-blooded animal a therapeutically effective amount of the compound as set forth in claim 1.

* * * * *